(12) United States Patent
Jugl et al.

(10) Patent No.: US 9,149,580 B2
(45) Date of Patent: Oct. 6, 2015

(54) CARTRIDGE HOLDER FOR A DRUG DELIVERY DEVICE

(75) Inventors: Michael Jugl, Frankfurt am Main (DE); Turhan Ergel, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/130,036

(22) PCT Filed: Jul. 16, 2012

(86) PCT No.: PCT/EP2012/063870
§ 371 (c)(1),
(2), (4) Date: Dec. 30, 2013

(87) PCT Pub. No.: WO2013/010973
PCT Pub. Date: Jan. 24, 2013

(65) Prior Publication Data
US 2014/0142515 A1    May 22, 2014

(30) Foreign Application Priority Data
Jul. 19, 2011   (EP) .................................. 11174477

(51) Int. Cl.
*A61M 5/315*   (2006.01)
*A61M 5/28*    (2006.01)
*A61M 5/24*    (2006.01)

(52) U.S. Cl.
CPC . *A61M 5/28* (2013.01); *A61M 5/24* (2013.01); *A61M 2005/2403* (2013.01); *A61M 2005/2407* (2013.01); *A61M 2005/2418* (2013.01); *A61M 2005/2437* (2013.01); *A61M 2005/2477* (2013.01); *A61M 2005/2481* (2013.01); *A61M 2005/2485* (2013.01)

(58) Field of Classification Search
CPC ............. A61M 2005/2403; A61M 2005/2418; A61M 2005/2477
USPC ......................................................... 604/218
See application file for complete search history.

(56) References Cited

U.S. PATENT DOCUMENTS 6,478,771 B1    11/2002   Lavi et al.
2006/0178631 A1 *  8/2006  Gillespie et al. .............. 604/139

FOREIGN PATENT DOCUMENTS

| DE | 1073156  | 1/1960  |
|----|----------|---------|
| EP | 0829268  | 3/1998  |
| WO | 01/32255 | 5/2001  |
| WO | 01/60311 | 8/2001  |
| WO | 01/74425 | 10/2001 |

OTHER PUBLICATIONS

International Search Report for Int. App. No. PCT/EP2012/063870, completed Aug. 21, 2012.

* cited by examiner

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

A cartridge holder for a drug delivery device is presented comprising a housing extending in an axial direction and being adapted to receive a cartridge at least partially filled with a medicament, said cartridge being sealed near a distal end by way of a pierceable seal. At least one bearing element is fixed to the housing, and at least one tensioning member is engaged with the bearing element and with the cartridge in an axial direction for transmitting a distally directed injection force from the cartridge to the housing.

16 Claims, 4 Drawing Sheets

CARTRIDGE HOLDER FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2012/063870 filed Jul. 16, 2012, which claims priority to European Patent Application No. 11174477.7 filed Jul. 19, 2011. The entire disclosure contents of these applications are herewith incorporated by reference into the present application.

TECHNICAL FIELD

The present invention relates to the field of drug delivery devices and in particular to those providing preparation and injection of a liquid medicament to a patient. Furthermore, the invention relates to a cartridge holder typically designed as a housing component of a drug delivery device, such as a pen-type injector. Such a cartridge holder is particularly adapted to accommodate and to hold a cartridge filled with the medicament to be injected.

BACKGROUND

User operated drug delivery devices are as such known in the art. They are typically applicable in circumstances, in which persons without formal medical training, i.e., patients, need to administer an accurate and predefined dose of a medicament, such as heparin or insulin. In particular, such devices have application, where a medicament is administered on a regular or irregular basis over a short term or long-term period.

In order to accommodate with these demands, such devices have to fulfill a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose. Moreover, the device should be suitable for recycling.

To meet these requirements, the number of parts required to assemble the device and the number of material types the device is made from need should be kept at a minimum.

The medicament to be dispensed by means of the drug delivery device is typically provided in a disposable or replaceable cartridge, such as a vial, an ampoule or a carpule comprising a slidably disposed piston to be operably engaged with a piston rod of a drive mechanism of the drug delivery device. By applying thrust to the cartridge's piston in distal direction, a predefined dose of the liquid drug can be dispensed and expelled from the cartridge.

Cartridges as they are commonly used with drug delivery devices are typically sealed by means of as sealing septum. Such a septum is usually designed as rubber stopper providing an air-tight seal but being pierceable by piercing elements such as injection needles or cannulae.

FIG. 5 shows an enlarged view of a typical configuration of a cartridge mounted in a cartridge holder. The cartridge 30 comprises a substantially cylindrically-shaped barrel 32 which in distal direction 48, pointing upwardly in the sketch of FIG. 5, is sealed by a penetrable or pierceable sealing element 42. The sealing element 42 almost covers the entire cross section of the head portion 40 of the barrel 32 and remains fixedly attached thereto by way of a beaded cap 41, typically made of aluminum.

A distal end face 24 of the cartridge holder is symbolized in FIG. 5 in cross section. Typically, the cartridge 30 is arranged inside the cartridge holder in such a way, that the septum 42 can be penetrated and pierced by an injection needle entering the cartridge holder via the central through opening 22 provided in the distal end face 24. Since a central through opening of the beaded cap 41 is typically aligned with the central through opening 22 of the distal end face 24, the piercing member may easily penetrate the septum 42.

The cartridge 30 is also sealed in proximal direction 50 by way of a piston slidably displaced inside the cartridge 30 in distal or proximal direction 48, 50. Since the medicament 34 contained in the cartridge may feature a certain viscosity and since injection needles designed to penetrate the septum 42 might be rather small in diameter, a substantial and considerable distally directed pressure has to be applied to the piston of the cartridge 30 in order to expel a predefined amount of the medicament via the distal end of the cartridge 30.

Even though the cartridge 30 may also be radially clamped between side wall section 25 of the cartridge holder, the distally directed dispensing force 52 may lead to a substantial compression 58 of the septum 42 in axial direction. Hence, during a dose dispensing action, the cartridge 30 may become subject to a distally directed displacement. After termination of a dispensing procedure, the elastic energy stored in the septum 42 may dissipate and the septum 42 may relax into its initial configuration.

Consequently, the vitreous body 32 of the cartridge 30 may become subject to a proximally directed displacement. Since the piston of the cartridge 30 is operably engaged with a drive mechanism of a drug delivery device, the piston may be hindered to follow the relaxation-induced proximal displacement of the cartridge 30. As a consequence, the piston moves in distal direction 48 relative to the vitreous body 32 of the cartridge 30, thus leading to a post-dispending droplet generation at the distal end of the injection needle. Also the central portion 44 of the septum 42 may bulge in distal direction 48 and may even extend through the central through opening of the beaded cap 41.

In case the injection needle has already been removed from the cartridge holder, the elastic relaxation behaviour of the septum 42 may lead to a considerable increase of fluid pressure inside the cartridge 30, which, during a repeated attachment of a piercing needle to the cartridge holder may lead to a respective droplet formation at the needle end.

Even though the cartridge would be sufficiently clamped in the housing, a respective fluid pressure may still built up when the septum 42 relaxes and axially expands in proximal direction 50.

Moreover, the axial displacement of the cartridge with respect to a cartridge holder is also disadvantageous in terms of dosing precision.

It is therefore an object of the present invention to provide a cartridge holder comprising beneficial properties in terms of dosing precision and reduced droplet generation. It is a further object of the invention to reduce mechanical stress and pressure acting on a septum of a cartridge during and after a dose dispensing procedure. The intended solution should be robust and failure safe. It should further be easy and cost-efficient to implement even with existing cartridge holder designs.

SUMMARY

The present invention provides a cartridge holder for a drug delivery device, in particular for a pen-type injector adapted to set and to dispense a pre-defined amount of a liquid medicament provided in a cartridge. The cartridge holder, which typically forms a housing component of the drug delivery device comprises a housing, preferably of elongated shape extending in an axial direction. The housing of the cartridge holder is particularly adapted to receive and to fix a cartridge being at least partially filled with a medicament to be dispensed and injected by means of the drug delivery device. The cartridge is sealed near a distal end by way of a pierceable seal, typically, by way of a septum to be penetrated by a double tipped injection needle or cannula.

The cartridge holder further comprises at least one bearing element which is fixed to the housing. The bearing element may be integrally formed with the housing, typically manufactured as an injection moulded plastic component. The bearing element may also be designed as a separate piece to be interconnected with the housing. It may also be designed as a particular portion of the housing of the cartridge holder. The cartridge holder according to the present invention further comprises at least one tensioning or clamping member, to engage with the bearing element and with a cartridge in an axial direction. By way of the at least one tensioning or clamping member, a distally directed injection force, typically exerted during a dose dispensing procedure can be transmitted or transferred from the cartridge to the housing by at least partially bypassing the septum of the cartridge.

Preferably, bearing element and tensioning member are designed and positioned such that the tensioning member engages with the body of the cartridge in a region spaced apart from the septum of the cartridge in proximal direction.

In particular, the at least one bearing element and the tensioning member of the cartridge holder are adapted to provided a force transmitting support established outside the region of the septum of the cartridge. In terms of a force flow, bearing element and tensioning member are designed such, that they provide a kind of force bypass. This way, an injection force transferred via the vitreous body of the cartridge may be at least partially but directly transferred to the cartridge holder via the tensioning member and the bearing element, thus reducing the force and pressure impact on the distally located septum of the cartridge.

By reducing mechanical impact and force effects on the septum, respective relaxation effects of the septum may decrease accordingly. As a consequence, axial cartridge displacement as well as post-dispending droplet generation can be advantageously reduced or even entirely eliminated.

According to a preferred embodiment, the housing of the cartridge holder comprises a distal socket portion being reduced in diameter compared to a proximal housing portion. Both, distal socket portion and proximal housing portion may feature a substantially cylindrical or at least circular geometry adapted to the overall cylindrical geometry of the cartridge to be placed therein. The at least one bearing element is arranged at the socket portion, at the proximal housing portion and/or between socket portion and proximal housing portion of the cartridge holder.

According to a further embodiment, the at least one bearing element extends inwardly from a side wall section of the cartridge holder housing. Typically, the bearing element is arranged at a particular axial position of the housing of the cartridge holder that corresponds with a recessed portion of the cartridge when mounted in the cartridge holder.

The tensioning member according to another preferred embodiment is attached to the bearing element and comprises a compression or a tension spring. Said compression or tension spring substantially extends in axial direction and engages with the body of the cartridge in axial, hence proximal or distal direction. The tensioning member according to another preferred embodiment is attached to the bearing element and comprises a rubber member or a foamed rubber member. Said rubber member or foamed rubber member substantially extends in axial direction and engages with the body of the cartridge in axial, hence proximal or distal direction.

Preferably, the tensioning member extends in proximal direction with a free end, so as to exert a proximally directed counterforce to the cartridge. The proximal extension of the tension or clamping member is particularly beneficial when the tensioning member comprises a compression spring that is to be compressed and to be biased in distal direction. Said spring element can then provide a proximally directed counterforce to act on the vitreous body of the cartridge in order to move the cartridge and its distally located septum away from a distal end face of the cartridge holder.

According to another preferred aspect, the at least one bearing element and the tensioning member are arranged and configured such that the free end of the tensioning member abuts against a radially widened shoulder portion of the cartridge in proximal direction. Said shoulder portion of the cartridge is typically positioned between a diameter-reduced distal head or neck portion of the cartridge and a proximal, substantially cylindrically-shaped radially widened body of the cartridge.

By arranging the at least one bearing element in the region of a stepped-down neck portion of the cartridge, the proximally extending tensioning member or spring element may directly engage with the radially widened shoulder portion of the cartridge.

According to a further aspect, the cartridge holder further comprises at least one counter-bearing element fixedly attached to its housing to provide an axial end stop for the cartridge. Generally, the counter-bearing element directly corresponds to the bearing element and may also serve to act as an axial support for a tensioning or clamping member. In fact, the counter-bearing element may directly engage with the body of the cartridge in order to clamp the cartridge in axial direction between the tensioning member and the counter-bearing element. Bearing element, counter-bearing element and tensioning member may therefore provide a tight fit for the cartridge in the cartridge holder.

In a further embodiment, the counter-bearing element is arranged at the housing to provide a proximal end stop for the cartridge. Also the counter-bearing element may be integrally formed with the housing of the cartridge holder. The counter-bearing element may for instance be arranged near a proximal end of the cartridge. By way of the bearing element and the tensioning member, e.g. adapted to act on the shoulder portion of the cartridge in proximal direction, the cartridge can be fixedly arranged and tightly clamped or fastened with respect to the cartridge holder at least in axial direction. In such a clamping configuration, the distal end of the cartridge, in particular its septum can be permanently kept substantially force-free.

According to an alternative embodiment, the counter-bearing element is arranged at the socket portion of the housing of the cartridge holder or at an adjacent shoulder portion of said housing to provide a proximal end stop for the cartridge. Here, the counter-bearing element is adapted to engage with the stepped-down neck portion or indentation of the body of the cartridge. Typically, the counter-bearing element may engage with the beaded cap of the cartridge in order to inhibit a proximally directed motion of the cartridge relative to the counter-bearing element and/or relative to the cartridge holder housing.

However, depending on the type of tensioning member used here, the counter-bearing element may also provide a distal end stop for either neck portion, shoulder portion or head portion of the cartridge. For instance, the tensioning member may serve to displace the cartridge in distal direction relative to the housing of the cartridge holder, thereby pressing the shoulder portion of the cartridge against a respective counter-bearing element in distal direction. Then, the position of the counter-bearing element preferably serves to provide that an axial gap is formed between the distal end faces of cartridge and cartridge holder.

According to a further embodiment, the axial distance between the bearing element and the counter-bearing element as well as the spring effect of the tensioning member is or are chosen such, that the tensioning member is tensioned or biased to a predefined degree when a cartridge with given dimensions is arranged in the housing.

In a further preferred aspect, a proximally directed counterforce to be provided by the biased or pre-tensioned tensioning member is substantially smaller than or equal to a distally directed dispensing force to be applied to the cartridge during a dose dispensing procedure. In such a configuration, the force effect acting on the septum of the cartridge during dose dispending can be at least reduced by the counterforce provided by the tension element. In embodiments, where the counterforce provided by the tensioning element does not exceed typical injection forces, the distal end of the cartridge, hence its beaded cap, beneficially buts with the inside of the distal end face of the cartridge holder in order to prevent substantial cartridge displacement during dose injection.

In a further configuration, e.g. when replacing the tensioning member by a spring member with a different, e.g. larger spring constant, the proximally directed counterforce provided by the tensioning member can be substantially larger than the distally directed dispensing force applied to the cartridge during a dose dispensing procedure. In particular, the tensioning member may be designed such that a respective counterforce even exceeds a maximum dispensing force at least by a given offset force. This way, the cartridge can be permanently clamped in axial direction inside the cartridge holder.

Then, under ordinary dispensing conditions the cartridge will not move at all with respect to the housing of the cartridge holder. Hence, septum deformation and respective relaxation can be entirely eliminated. With such an embodiment, the cartridge can be arranged in the cartridge holder, such that an axial gap is provided between the distal end faces of cartridge and cartridge holder. At least, the head portion of the cartridge can in principal be kept in a non-contacting configuration with respect to the distal end face of the cartridge holder.

Moreover, according to an additional or alternative embodiment, bearing and counter-bearing element may be arranged such that their axial distance is slightly smaller than the respective axial dimensions of the cartridge. Hence, the tensioning element may then be realized by a specific arrangement of bearing and counter-bearing element.

It is further to be mentioned, that the bearing element as well as the tensioning member may comprise different shapes and designs. The bearing and/or counter-bearing element may comprise radially inwardly protruding struts but may also feature a single or multiple circumferentially extending radially inwardly protruding ribs. Accordingly, the tensioning member may comprise one or several compression or tension springs arranged at selected positions along the circumference of the housing of the cartridge holder. Moreover, the tensioning member may comprise a single or a plurality of helical-shaped or helically wounded compression springs having a diameter that substantially matches with the diameter of the bearing element or with the lateral distance of bearing elements arranged along the circumference of the housing of the cartridge holder.

In a further and independent aspect, the invention also relates to a drug delivery device for dispensing a predefined amount of a medicament. The drug delivery device, typically designed as pen-type injector comprises a cartridge holder as described above and a body that provides a housing for a drive mechanism. Cartridge holder and body are inter-connectable with each other. The drive mechanism typically comprises a piston rod to become operably engaged with the piston of the cartridge. The cartridge holder is adapted to receive and to fix the cartridge which is to be operably engaged with the drive mechanism, in particular with the piston rod. By having the cartridge and with its movable piston fixedly arranged in the cartridge holder, the drive mechanism can be operated to exert distally directed thrust to the piston in order to expel a predefined amount of the medicament from the cartridge through a pierceable and distal seal of the cartridge.

It is to be noted here, that the cartridge holder is particularly designed for drug delivery devices such as pen-type injectors. However, the invention is not generally limited to such devices but may be universally applied with other drug delivery devices, such like infusers or injection pumps.

In a further preferred aspect, the drug delivery device comprises a cartridge being at least partially filled with the medicament and being arranged in the cartridge holder. Preferably, the drug delivery device and the cartridge mounted therein are designed as disposable devices or components. Hence, after consumption of the medicament provided in the cartridge, the entire device is intended to be discarded rather than to replace the empty cartridge.

BRIEF DESCRIPTION OF THE DRAWINGS

In the following, preferred embodiments of the invention will be described in detail by making reference to the drawings in which.

DETAILED DESCRIPTION

Figure 1:
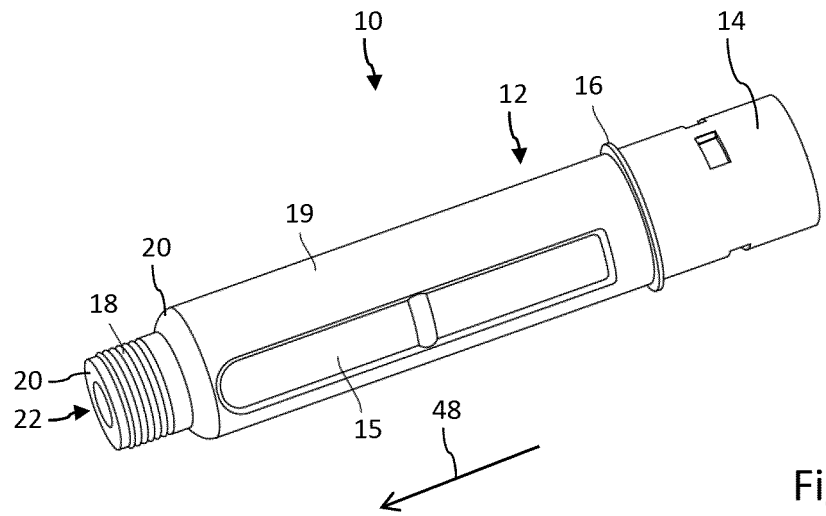
FIG. 1 shows a perspective and isolated view of a cartridge holder.

The cartridge holder 10 as illustrated in FIG. 1 comprises a tubular-shaped housing 12 having a proximal portion 19, a shoulder portion 20 and a distally located socket portion 18. The threaded socket portion 18 is adapted to threadedly receive a needle assembly having an injection needle to penetrate the septum 42 of the cartridge 30 shown in FIGS. 2 to 4.

Figure 2:
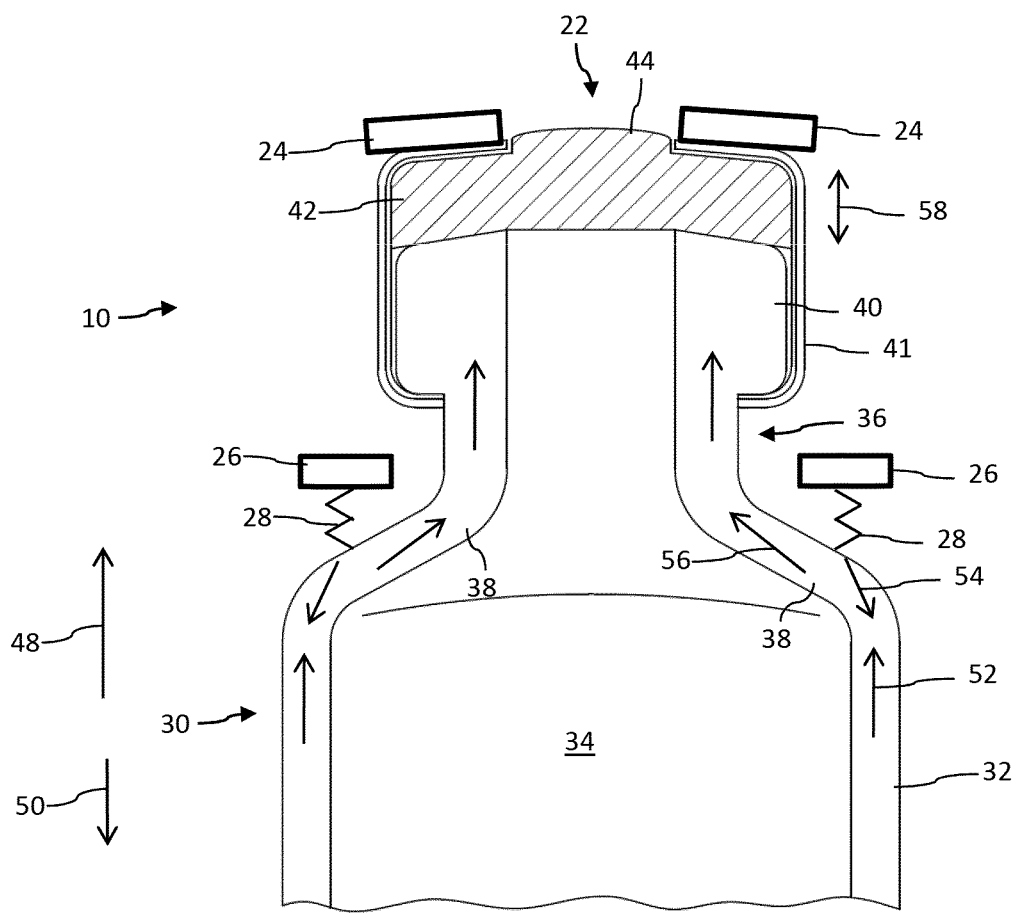
FIG. 2 schematically illustrates the mechanical principle of the present invention according to a first embodiment in cross section.
Figure 3:
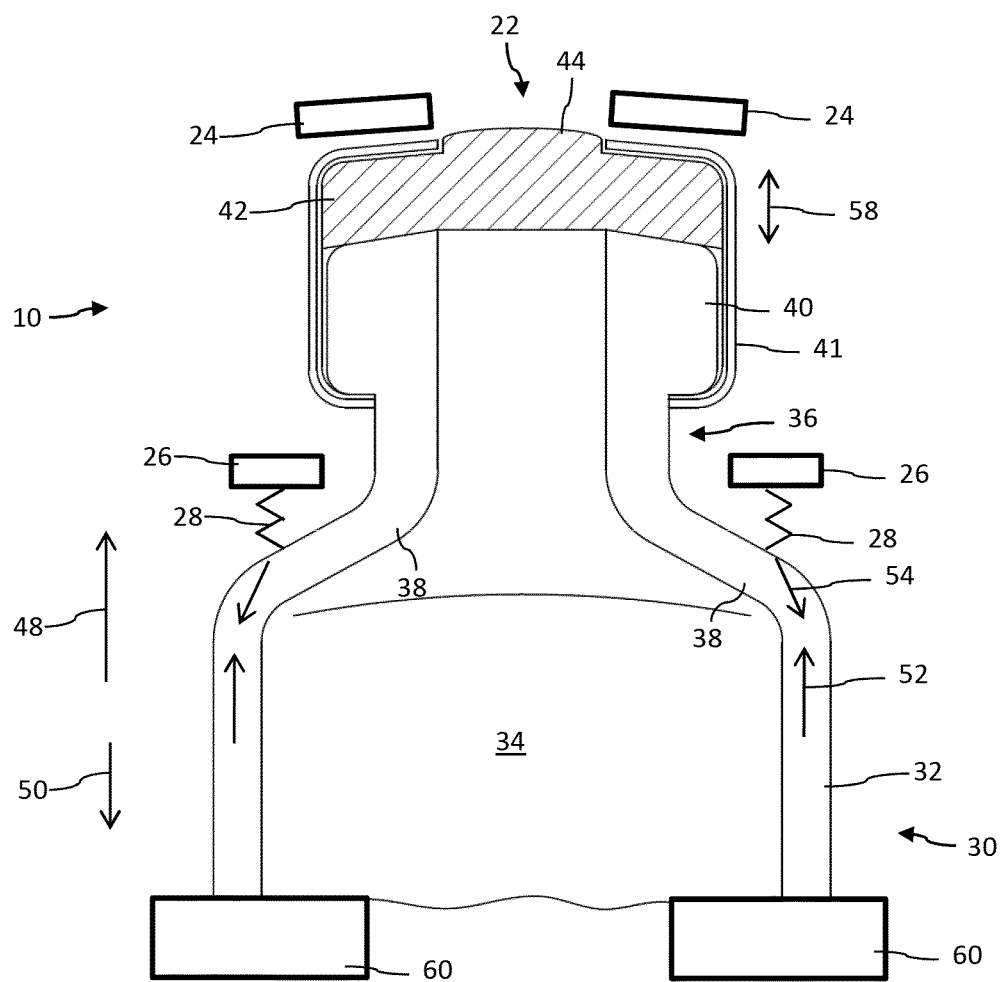
FIG. 3 is illustrative of a further embodiment of the invention making use of a counter-bearing element.
Figure 4:
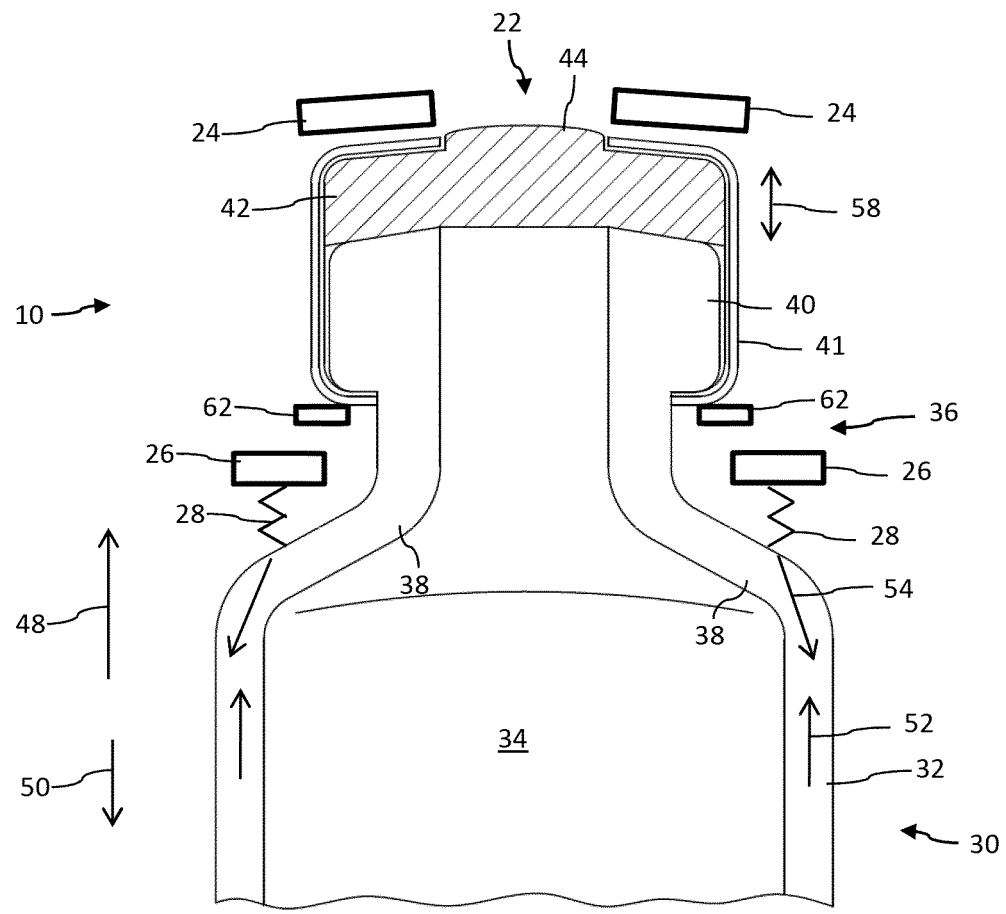
FIG. 4 shows another embodiment making use of a counter-bearing element.
Figure 5:
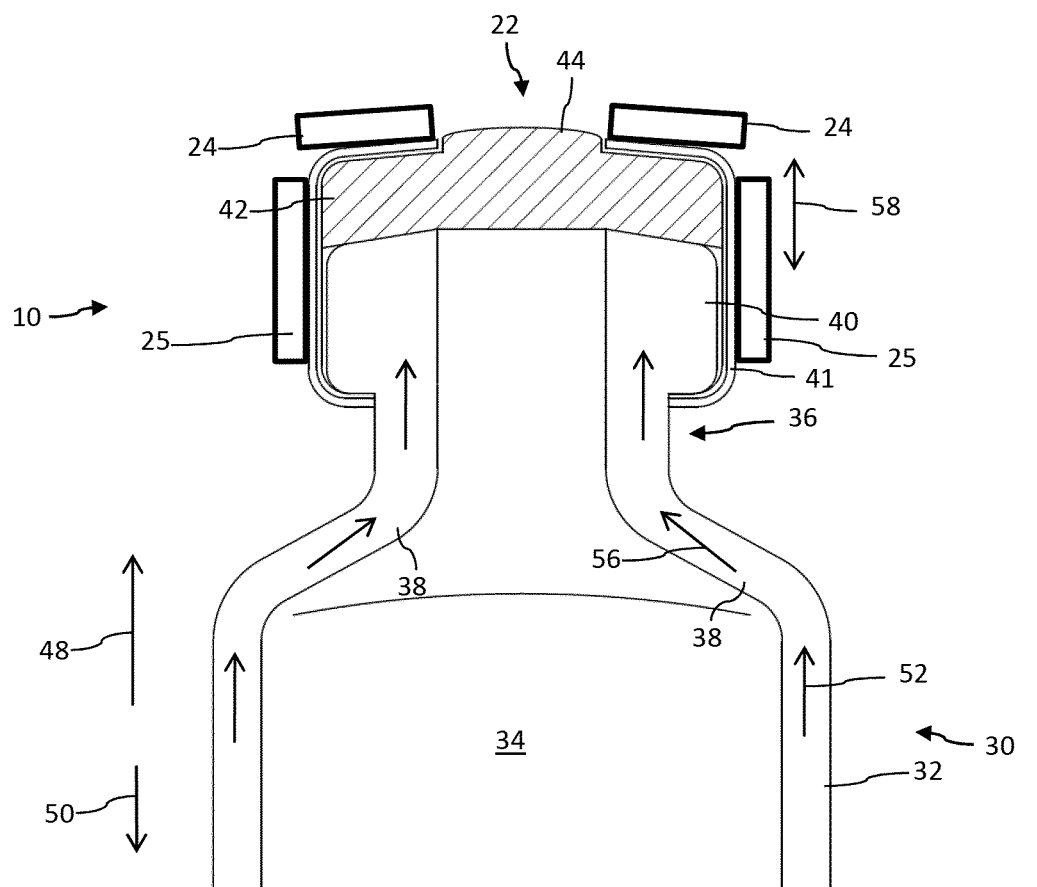
FIG. 5 illustrates known solutions according to the prior art.

The distal end face 24 of the socket portion 18 of the cartridge holder 10 is exemplary illustrated in FIGS. 2 to 4 in cross section. The tubular-shaped proximal housing portion 19 of the cartridge holder 10 further comprises inspection windows 15 allowing to visually inspect the filling level of the cartridge 30 disposed therein. Furthermore, towards a proximal section, the cartridge holder 10 comprises an insert piece 14 which is adapted to mate with a correspondingly shaped receptacle of a proximal housing component of the drug delivery device, which is not explicitly illustrated here. The circumferential rim 16 serves as a stopper when cartridge holder 10 and body of the drug delivery device are interconnected.

In the present terminology, distal direction 48 points towards the outlet end of the cartridge holder, hence towards the patient whereas proximal direction 50 points in the opposite direction, away from the patient.

The cross-sectional schematic views according to FIGS. 2 to 4 illustrate the bearing element 26 radially inwardly protruding from a not further illustrated side wall section of the cartridge holder 10. The bearing element 26 serves as an axial support for an axially extending compression spring 28, adapted to directly but with a radially widening shoulder portion 38 of a bottle-necked body 32 of the cartridge 30. Since the bearing element 26 is either fixedly attached to the housing 12 of the cartridge holder 10 or is even integrally formed therewith, the cartridge 30 can be displaced and biased in proximal direction 50 away from the distal end face 24 of the cartridge holder 10.

This way, an injection force 56 effective on the distally located septum 42 may be remarkably reduced compared to the initially applied injection force 52. Said forces 56, 52 may at least differ by the counterforce 54, exerted by the compression spring 28 in proximal direction. Tensioning member 28 and bearing element 26 may therefore absorb at least a part of the initially applied injection force 52 acting on the piston and therefore on the body 32 of the cartridge 30. Axial compression or expansion 58 of the septum 42 can be therefore remarkably reduced. As further illustrated in FIG. 2, the distal end of the cartridge 30 typically gets in direct contact with the distal end face 24 of cartridge holder. Such an arrangement of the cartridge 30 is particularly beneficial when the counterforce 54 provided by the tensioning element 26 is smaller than the injection force 52 transferred via the body 32 of the cartridge 30.

Moreover, as becomes apparent from the sketches of FIGS. 2 to 4, by way of the tensioning member 28 also a tolerance elimination of the cartridge 30 can be generally provided. Typically, cartridges 30 comprise a vitreous body 32, made of glass. Due to inevitable inadequacies of the manufacturing process of such bodies 32, the cartridges 30 may comprise outer dimensions within a certain tolerance regime. By supporting the cartridge 30 in a kind of spring or clamping mechanism in the cartridge holder, such manufacturing tolerances can be easily compensated.

It is of general benefit in all embodiments according to FIGS. 2 to 4, that the bearing element 26 and the tensioning member 28 provide axial support for the cartridge 30 without interacting with its head section 40 or with its septum 42.

In the embodiment according to FIG. 3, the cartridge holder 10 is further equipped with at least one counter-bearing element 60 adapted to provide a proximal end stop for the cartridge 30. In the present context a proximal end stop delimits and inhibits proximally directed displacement of the cartridge 30 beyond said stop or counter-bearing element 60. In the embodiment according to FIG. 3, the cartridge 30 can be effectively clamped between bearing element 26, counter-bearing element 60 and the compression spring 28.

Also here, it would be conceivable to have the compression spring arranged exclusively or additionally at the counter bearing element 60. Depending on a required predefined pretension, the compression spring 28 has to be compressed in order to arrange the cartridge 30 between the bearing element 26 and the counter-bearing element 60. It is further conceivable, that the cartridge 30 as a whole is displaced and pressed against the counter-bearing element 60 or elements in proximal direction 50 in such a way, that the distal end of the beaded head 40 of the cartridge is no longer in abutment with the distal end face 24 of the cartridge holder 10. Even an axial gap between cartridge holder 10 and cartridge 30 may evolve.

Furthermore, if the pretension of the compression spring 28 and the respective counterforce 54 acting on the body 32 in proximal direction 50 is substantially larger than an expected and distally directed injection force 52, the cartridge 30 may no longer move relative to the housing 1 of the cartridge holder 10 during a dose dispensing action. As a consequence, the force flow of the injection force 52 will be entirely transferred through the tensioning member 28 and the bearing element 26 to the housing 12 of the cartridge holder 10. In effect, the force flow will almost completely bypass or circumvent the septum 42.

The embodiment as depicted in FIG. 4 shows an alternative way on how to provide a counter-bearing element 62. Here, the counter-bearing element 62 is located in close axial proximity to the bearing element 26. Also here, the counter-bearing element acts as a proximal end stop and engages with the stepped-down neck portion 36 of the body 32 of the cartridge 30. As illustrated, the radially widened head 40 covered with a beaded cap 41 and forming an undercut, buts against the distally facing support face of the counter bearing element 62. The compression spring 28 arranged between the shoulder portion 38 of the vitreous body 32 and the radially inwardly protruding bearing element 26 serves to keep the cartridge 30 in the position as illustrated in FIG. 4.

The invention claimed is:

1. A cartridge holder for a drug delivery device, comprising:
   a housing extending in an axial direction and being adapted to receive a cartridge at least partially filled with a medicament, said cartridge being sealed near a distal end by way of a pierceable seal,
   at least one bearing element fixed to the housing, and
   at least one tensioning member to engage with the bearing element and with the cartridge in an axial direction for transmitting a distally directed injection force from the cartridge to the housing.

2. The cartridge holder according to claim 1, wherein the housing comprises a distal socket portion reduced in diameter compared to a proximal housing portion, wherein the at least one bearing element is arranged at the socket portion, at the proximal housing portion and/or between socket portion and proximal housing portion.

3. The cartridge holder according to claim 1, wherein the bearing element extends inwardly from a side wall section of the housing.

4. The cartridge holder according to claim 1, wherein the tensioning member attached to the bearing element comprises a compression spring or a tension spring and extends substantially in axial direction.

5. The cartridge holder according to claim 4, wherein the tensioning member extends in proximal direction with a free end.

6. The cartridge holder according to claim 1, wherein the at least one bearing element and the tensioning member are arranged such that the free end of the tensioning member buts against a radially widened shoulder portion of the cartridge in proximal direction.

7. The cartridge holder according to claim 1, further comprising at least one counter-bearing element fixedly attached to the housing to provide an axial end stop for the cartridge.

8. The cartridge holder according to claim 7, wherein the counter-bearing element is arranged at the housing to provide a proximal end stop for the cartridge.

9. The cartridge holder according to claim 7, wherein the counter-bearing element is arranged at the socket portion or at an adjacent shoulder portion of the housing to provide a proximal end stop for the cartridge.

10. The cartridge holder according to claim 7, wherein the counter-bearing element provides a distal end stop for neck or head portion of the cartridge.

11. The cartridge holder according to claim 1, wherein the axial distance between the bearing element and the counter-bearing element is chosen such that the tensioning member is tensioned to a predefined degree when a cartridge with pre-defined dimensions is arranged in the housing.

12. The cartridge holder according to claim 11, wherein a proximally directed counterforce provided by the biased tensioning member is substantially smaller than or equal to a distally directed dispensing force to be applied to the cartridge during a dose dispensing procedure.

13. The cartridge holder according to claim 11, wherein the proximally directed counterforce is substantially larger than the distally directed dispensing force to be applied to the cartridge during a dose dispensing procedure.

14. The cartridge holder according to claim 1 wherein the housing comprises a distally located socket portion with an outer thread to threadedly receive a needle assembly having an injection needle to penetrate the pierceable seal of the cartridge when assembled inside the housing.

15. A drug delivery device for dispensing a pre-defined amount of a medicament, the device comprising:
a cartridge holder according to claim 1,
a body inter-connectable with the cartridge holder; and
a drive mechanism disposed in the body and being adapted to operably engage with a piston of a cartridge mounted in the cartridge holder to expel a predefined amount of the medicament from the cartridge.

16. The drug delivery device according to claim 11, further comprising a cartridge at least partially filled with the medicament and being arranged in the cartridge holder.

* * * * *